United States Patent
Yan et al.

(10) Patent No.: US 10,195,155 B2
(45) Date of Patent: Feb. 5, 2019

(54) DRUG CARRIER FOR TUMOR-SPECIFIC TARGETED DRUG DELIVERY AND USE THEREOF

(71) Applicant: Institute of Biophysics, Chinese Academy of Sciences, Beijing (CN)

(72) Inventors: Xiyun Yan, Beijing (CN); Kelong Fan, Beijing (CN); Minmin Liang, Beijing (CN); Fei Wang, Beijing (CN); Demin Duan, Beijing (CN); Dexi Zhang, Beijing (CN); Jing Feng, Beijing (CN); Dongling Yang, Beijing (CN)

(73) Assignee: Institute of Biophysics, Chinese Academy of Sciences, Beijing (CN)

( * ) Notice: Subject to any disclaimer, the term of this patent is extended or adjusted under 35 U.S.C. 154(b) by 0 days.

(21) Appl. No.: 15/314,307

(22) PCT Filed: Sep. 24, 2014

(86) PCT No.: PCT/CN2014/087286
§ 371 (c)(1),
(2) Date: Nov. 28, 2016

(87) PCT Pub. No.: WO2015/180325
PCT Pub. Date: Dec. 3, 2015

(65) Prior Publication Data
US 2017/0189343 A1    Jul. 6, 2017

(30) Foreign Application Priority Data
May 28, 2014 (CN) .......................... 2014 1 0230829

(51) Int. Cl.
| *A61K 9/51* | (2006.01) |
| *A61K 31/70* | (2006.01) |
| *A61K 47/42* | (2017.01) |
| *A61K 47/64* | (2017.01) |
| *A61K 47/69* | (2017.01) |

(52) U.S. Cl.
CPC ............... *A61K 9/51* (2013.01); *A61K 31/70* (2013.01); *A61K 47/42* (2013.01); *A61K 47/64* (2017.08); *A61K 47/6925* (2017.08)

(58) Field of Classification Search
CPC .......... A61K 31/70; A61K 47/42; A61K 9/51
See application file for complete search history.

(56) References Cited

FOREIGN PATENT DOCUMENTS

| CN | 101942022 A | 1/2011 | |
| CN | 101942022 * | 1/2012 | ............. A61K 47/42 |
| CN | 104013599 A | 9/2014 | |

OTHER PUBLICATIONS

Kelong Fan et al. (WIREs nanomed Nanobiotechnol 2013, 5:287-298. Doi 10.1002/wnan.1221) (Year: 2013).*
"International Application No. PCT/CN2015/074994, International Search Report dated Mar. 4, 2015", w/ English Translation, (dated Mar. 4, 2015), 5 pgs.
"International Application No. PCT/CN2015/074994, Written Opinion dated Mar. 4, 2015", (dated Mar. 4, 2015), 4 pgs.

* cited by examiner

*Primary Examiner* — Anna R Falkowitz
(74) *Attorney, Agent, or Firm* — Schwegman Lundberg & Woessner, P.A.

(57) ABSTRACT

The present disclosure relates to a tumor-targeted drug delivery system, comprising a tumor-targeted drug carrier and a tumor-treating drug, wherein the tumor-targeted drug carrier comprises full heavy-chain human ferritin. The present disclosure also relates to a method for preparing the tumor-targeted drug delivery system comprising: depolymerizing a polymerized full heavy-chain human ferritin; adding a tumor-treating drug to the depolymerized full heavy-chain human ferritin so as to bind the tumor-treating drug to the depolymerized full heavy-chain human ferritin; and re-polymerizing the depolymerized full heavy-chain human ferritin bound with the tumor-treating drug to form a nanoparticle.

8 Claims, 6 Drawing Sheets

DRUG CARRIER FOR TUMOR-SPECIFIC TARGETED DRUG DELIVERY AND USE THEREOF

PRIORITY APPLICATIONS

This application is a U.S. National Stage Filing under 35 U.S.C. 371 from International Application No. PCT/CN2014/087286, filed on 24 Sep. 2014, and published as WO2015/180325 on 3 Dec. 2015, which claims the benefit of priority to Chinese Application No. 201410230829.0, filed on 28 May 2014; which applications and publication are incorporated herein by reference in their entirety.

TECHNICAL FIELD

The disclosure relates to an interdisciplinary field of nanotechnology, bionics, immunology, and biomedicine. Particularly, the disclosure relates to a tumor-targeted drug delivery system, comprising a tumor-targeted drug carrier and a tumor-treating drug, wherein the tumor-targeted drug carrier comprises full heavy-chain human ferritin. The disclosure further relates to a method for preparing the tumor-targeted drug delivery system.

BACKGROUND ART

Cancer has become one of main diseases which are increasingly common and severely threaten human lives and life quality. As aged population continuously increases, it is predicted that the occurrence of cancer will continue to increase. At present, there are mainly three kinds of methods for treating cancer, including surgery, radiation therapy, and chemotherapy. The selection of therapeutic means of cancer depends on the type, the site, and the spreading of cancer. Chemotherapy is a therapeutic means, which uses chemical drugs to kill tumor cells. It is a systemic therapeutic means, and has therapeutic effect on all of primary lesions, metastatic lesions, and subclinical metastatic lesions. As for cancers, which will not be subjected to surgery and radiation therapy, only chemotherapy can be relied on. At present, clinically commonly-used chemotherapeutic anti-cancer drugs have severe side effects due to lack of targeting. These side effects usually limit applications of chemotherapeutic drugs and results in loss of therapeutic options for many cancers. For example, severe side effects, which are caused by non-specific toxicities from most of anthracycline antineoplastic drug molecules and platinum-containing substances, greatly limit the use of these chemotherapeutic drugs. Therefore, the development of a drug carrier, which is capable of specifically targeting tumor tissues and reducing toxic and side effects, is a challenge urgent to be solved in the field of cancer therapy.

SUMMARY OF THE INVENTION

An ideal drug carrier for the treatment of tumors should have the following characteristics: specifically targeting tumor cells or tumor tissues; capable of loading a high dosage of a therapeutic drug, capable of releasing the drug in tumor cells or allowing the drug to act on tumor cells; stable under physiological conditions; having good distribution and metabolic characteristics in body as well as excellent biocompatibility. However, it is very challenging to integrate all of these characteristics into one nanomaterial. Previous study of our laboratory indicated that human H-ferritin may specifically target common solid tumor tissues in human body, such as lung cancer, breast cancer, prostate cancer, cervical cancer, colorectal cancer, ovarian cancer, esophageal cancer, gastric cancer, thymic cancer, etc., and malignantly cancerous blood cells such as T lymphatic leukemia, erythroleukemia, etc., by binding its receptor, transferrin receptors 1 (TfR1), without modification or labeling with any specific ligand (Fan et al., Nature Nanotech. 2012; Chinese patent application 201110122433.0). Furthermore, H-ferritin has an outer diameter of 12 nm and a uniform particle size, and has a strong effects of penetration and retention in a tumor site (Dreher, M. R. et al., J Natl Cancer I, 2006). Therefore, human H-ferritin has a better targeting to tumors in bodies via both active targeting and passive targeting. An H-ferritin nanoparticle has a cavity of a diameter of 8 nm, and small molecule drugs may be loaded into the cavity by depolymerization-polymerization of the protein shell. Researchers have found that after binding to TfR1 on a tumor cell, H-ferritin nanoparticles would be transported into endosome and finally into lysosome. This enables H-ferritin, as a drug carrier, to deliver a drug into the interior of a cell to exert killing effect on a tumor cell. More importantly, human H-ferritin is an iron-storing protein naturally present in human bodies, and thus it has natural biocompatibility and low immunoreactivity to which those of other synthetic materials are not comparable. In addition to this, it is convenient for human H-ferritin to be expressed in a large amount in E. coli, and it may be rapidly and conveniently purified by means of using its property of high-temperature resistance (75° C.). In view of these characteristics of human H-ferritin, as a drug carrier itself, it is an ideal biological nonmaterial which integrates various advantages.

An object of the disclosure is to provide a novel protein-type tumor-specific targeted nanocarrier for chemotherapeutic drugs and uses thereof.

The drug carrier provided by the disclosure is a protein shell nanoparticle, which is naturally present in human bodies, can specifically recognize tumor tissues and cells, can enter lysosomes in cells, and release anti-tumor active drugs loaded therein.

The protein shell of the disclosure may be a genetically recombinant or natural apoferritin. Apoferritin is self-assembled from 12 or 24 heavy chain subunits and light chain subunits at any ratio. Natural apoferritin may be derived from eukaryotes, prokaryotes, or mammals.

The protein shell of the disclosure may also be a heat shock protein (HSP), a Dps (DNA protection during starvation) protein, or a viral protein shell having a nanoscale cavity structure.

The protein shell of the disclosure may be chemically coupled or genetically fused to targeting molecules such as antibodies, polypeptides, or nucleic acid aptamers, or signal molecules such as fluorescent molecules, radioactive nuclides.

The anti-tumor active drug loaded in the protein shell of the disclosure may be selected from chemotherapeutic drugs, radioisotopes, cytokines, nucleic acids, anti-tumor drugs, or anti-inflammatory drugs.

The protein-type targeting nanoscale drug carrier of the disclosure particularly refers to recombinant full heavy-chain human ferritin (H-ferritin). This ferritin shell can specifically bind to tumor cells and tumor tissues without modification of targeting molecules such as antibodies, polypeptides, and can enter tumor cells after binding to its receptor TfR1.

There may be two drug loading modes for the protein-type tumor-targeted nanoscale drug carrier of the disclosure:

an anti-tumor active small molecule drug, after binding to a metal ion, enter the inside of a protein shell through metal ion channels on the protein shell; and, an anti-tumor drug is added during the polymerization of a protein shell in the process of depolymerization-polymerization of the protein shell by means of pH or urea to achieve loading of the drug in the protein shell.

Tumor diseases, on which the protein-type tumor-targeted nanoscale drug carrier of the disclosure have an effect, are malignant tumors and cancers of human bodies, and among these, colorectal cancer, lung cancer, breast cancer, ovarian cancer, and melanoma are preferred. Particularly preferred are solid tumors of human bodies (for example, lung cancer, ovarian cancer, breast cancer, gastrointestinal cancer, colon cancer, pancreatic cancer, bladder cancer, renal cancer, prostate cancer, brain cancer, etc.) and various hematological cancers (for example, Hodgkin's disease, non-Hodgkin's lymphoma, leukemia, etc.).

The protein-type tumor-targeted nanoscale drug carrier of the disclosure may be administered to a patient suffering from a malignant tumor through intravenous, subcutaneous, intraarterial, or topical administration.

The protein-type tumor-targeted nanoscale drug carrier and its anti-tumor use of the disclosure have great social and economic benefits, and also have a good application prospect.

More specifically, the disclosure provides the following:

1. A tumor-targeted drug delivery system, comprising a tumor-targeted drug carrier and a tumor-treating drug, wherein the tumor-targeted drug carrier comprises full heavy-chain human ferritin.

2. The system according to 1, wherein the full heavy-chain human ferritin is polymerized to form a nanoparticle having a cavity, and the tumor-treating drug is loaded in the cavity.

3. The system according to 2, wherein the system is prepared by:

depolymerizing a polymerized full heavy-chain human ferritin;

adding the tumor-treating drug to the depolymerized full heavy-chain human ferritin so as to bind the tumor-treating drug to the depolymerized full heavy-chain human ferritin; and re-polymerizing the depolymerized full heavy-chain human ferritin bound with the tumor-treating drug to form a nanoparticle.

4. The system according to 3, wherein the full heavy-chain human ferritin is depolymerized under a condition of a high concentration of urea, and the depolymerized full heavy-chain human ferritin is re-polymerized by using a gradient of the concentration of urea gradually decreasing to zero.

5. The system of any of 1-4, wherein the tumor-treating drug is used for the treatment of malignant tumors and cancers of human bodies, and is preferably used for the treatment of colorectal cancer, lung cancer, breast cancer, ovarian cancer, melanoma, gastric cancer, pancreatic cancer, bladder cancer, renal cancer, prostate cancer, brain cancer and various hematological cancers such as Hodgkin's disease, non-Hodgkin's lymphoma, and leukemia.

6. The system according to 5, wherein the tumor-treating drug is used for the treatment of colorectal cancer.

7. The system of any of 1-4, wherein the tumor-treating drug is selected from chemotherapeutic drugs, radioisotopes, cytokines, nucleic acids, anti-tumor drugs, or anti-inflammatory drugs, and for example is Doxorubicin.

8. The system of any of 1-4, wherein the system is administered to a patient in need thereof in an intravenous, subcutaneous, intraarterial, or topical manner.

9. A method for preparing a tumor-targeted drug delivery system, comprising:

depolymerizing a polymerized full heavy-chain human ferritin;

adding a tumor-treating drug to the depolymerized full heavy-chain human ferritin so as to bind the tumor-treating drug to the depolymerized full heavy-chain human ferritin; and re-polymerizing the depolymerized full heavy-chain human ferritin bound with the tumor-treating drug to form a nanoparticle.

10. A tumor-targeted drug carrier, comprising full heavy-chain human ferritin.

11. Use of full heavy-chain human ferritin as a tumor-targeted drug carrier.

BRIEF DESCRIPTION OF THE DRAWINGS

FIG. 1a is a schematic diagram of the process for loading a drug Doxorubicin (Dox) to a tumor-targeted nanoscale drug carrier H-ferritin (HFn); FIG. 1b is a cryo-electron microscopy characterization graph of the drug carrier before and after loading Doxorubicin; FIG. 1c is dynamic light scattering characterization particle size profile before and after loading Doxorubicin.

FIG. 2a is the stability of a nanocarrier loaded with a drug (HFn-Dox) under conditions of physiological saline and normal mouse serum; FIG. 2b is the drug release profile of HFn-Dox under an acidic condition (pH=5) and a neutral condition (pH=7.4).

FIG. 3a shows the specific binding of fluorescence-labeled HFn protein and HFn-Dox to tumor cells; FIG. 3b shows that the specific binding of HFn protein with a tumor cell may be specifically competitively inhibited by HFn protein or HFn-Dox. However, there is substantially no difference with respect to inhibition curves. FIG. 3c shows that an anti-TfR1 antibody may specifically block the binding of HFn-Dox with a tumor cell. FIG. 3d is specific targeting imaging of tumors by radiolabeled HFn-Dox nanoparticles in vivo.

FIG. 5a is a study on the drug half-life of HFn-Dox nanoparticles and Free Dox; FIGS. 5b and 5c are studies on accumulated amounts of HFn-Dox nanoparticles and a Free Dox drug in a tumor tissue and a heart tissue respectively; FIG. 5d is a study on the removal in vivo of HFn-Dox nanoparticles and Free Dox.

FIG. 6a is inhibition curves of tumor growth; FIG. 6b is statistic results of survival times of tumor-bearing mice; FIG. 6c is body weight changes of tumor-bearing mice after administration.

DESCRIPTION OF EMBODIMENTS

The contents of the disclosure will be specifically illustrated with Examples below, but these Examples should not be construed as limiting the disclosure in any sense. Through wide and intensive studies by the inventor, human H-ferritin recombinantly expressed using a method of genetic engineering is used in the diagnosis and treatment of cancer, on the basis of preliminary work in this laboratory (Fan et al., Nature Nanotech. 2012) and Chinese invention patent application 201110122433.0. On this basis, the disclosure is completed.

Example 1. Preparation and Characterization of Tumor-Targeted Nanoscale Drug Carrier HFn-Dox As a drug carrier, it is the issue of drug loading that is to be first solved. As described, it is a common way at present to load a drug to a protein cavity by depolymerization-polymerization of a protein shell under the control of pH value. Actually, H-ferritin will be depolymerized under the condition of pH=2 due to its stability. With processing the protein shell of ferritin under such a strongly acidic condition, subunits of ferritin will not be perfectly re-assembled into the original protein shell when pH value is restored to a neutral condition, but some "indentations" will be caused (Kim, M. et al., *Biomacromolecules*, 2011). This will result in instable ferritin nanoparticles and decreased yield rate of drug packing after the drug is loaded. Furthermore, the targeting of the protein shell to tumors will be influenced due to the incompleteness thereof. Another method for loading a drug into ferritin is using metal ions as an auxiliary material for drug addition and passing a chemotherapeutic drug into a protein shell using a hydrophilic channel on the protein shell of ferritin after binding to the metal ions. Although a drug will be loaded into the protein shell using this method, metal ions will be introduced at the meanwhile and most of them are heavy metal elements. After a drug is loaded using this method, the burden on metabolic organs will be increased when treating tumor, resulting in heavy metal poisoning. In order to solve the problem of loading drugs, a relatively mild method of urea denaturation and renaturation is use in the disclosure to successfully prepare an H-ferritin-Doxorubicin nanoparticle (HFn-Dox) with a high loading amount. Depolymetization of the human H-ferritin shell is achieved under a condition of a high concentration of urea (for example, greater than 6M), and Doxorubicin (Dox) is added to the solution at the meanwhile. Loading of Dox into the human H-ferritin is achieved using a method of gradient urea dialysis. Since Dox has a $pK_a$ value of 8.2 (Yang, S. C. et al., *J Appl Polym Sci*, 2000), Dox molecules may be packaged in the H-ferritin shell by means of electrostatic adsorption effect between Dox molecules and the inner surface of H-ferritin shell in the process of depolymerization-polymerization of the H-ferritin shell (Harrison, P. M. & Arosio, P. *Biochim Biophys Acta*, 1996). It is identified by a method such as cryo-electron microscopy, dynamic light scattering, etc., that the structure of the human H-ferritin nanoparticle does not change before and after loading Dox. A specific example was as follows:

First, full length primers of human H-ferritin was designed using cDNA of a Hela cell line which highly expresses H-ferritin as a template, and cDNA of human H-ferritin (ATGACGACCGCGTCCACCTCGCAGGT-GCGCCAGAACTACCACCAGGACTCAGAGG CCGC-CATCAACCGCCAGATCAACCTGGAGCTCTACGC-CTCCTACGTTTACCTGTCCAT GTCTTACTACTTTGACCGCGATGATGTGGCCTT-GAAGAACTTTGCCAAATACTTTCTT CACCAATCT-CATGAGGAGAGGGAACATGCTGAGAAACTGAT-GAAGCTGCAGAACCA ACGAGGTGGCCGAATCTCCTCAGGATAT-CAAGAAACCAGACTGTGATGACTGGG AGAGCGGGCTGAATGCGATGGAGTGTGCATTA-CATTTGGAAAAAAATGTGAATCAGT CACTACTG-GAACTGCACAAACTGGCCACTGACAAAAATGAC-CCCCATTTGTGTGAC TTCATTGAGACACATTACCTGAATGAGCAGGT-GAAAGCCATCAAAGAATTGGGTGAC CACGTGAC-CAACTTGCGCAAGATGGGAGCGCCCGAATCCG-GCTTGGGGAATATCT CTTTGACAAGCACACCCTGGGAGACAGTGATAAT-GAAAGCTAG, 552 bp) was constructed onto an expression vector pET30A (Novagen); Next, Hfn-pET30a was transformed into an expression strain BL21 (DE3) (Novagen) using a prokaryotic expression system and expression was induced with IPTG, and human HFn protein was then purified (with respect to molecule construction, expression, and purification of human H-ferritin, see Fan et al., *Nature Nanotech.* 2012 and Chinese invention patent application 20111022433.0).

Figure 1:
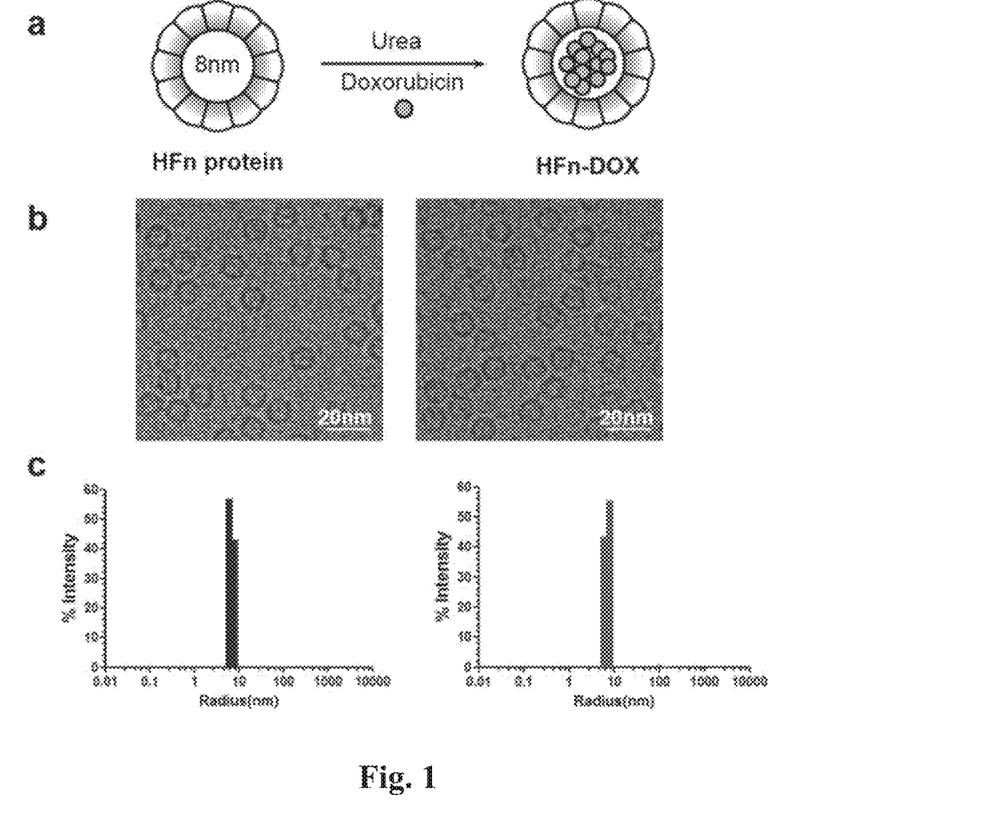
FIG. 1 shows the preparation and characterization of a tumor-targeted nanoscale drug carrier.

Thereafter, human HFn protein was added to 8 mol/L urea until the final concentration was 1 mg/mL. Reaction was performed at room temperature for 30 min to allow the HFn protein shell to be thoroughly depolymetized. A Doxorubicin agent was then added until the final concentration was 1 mg/mL. After reaction was performed for 10 minutes under protection from light, reaction liquid was transferred to a dialysis bag with a molecular weight cutoff of 3 kDa. The reaction liquid was then subjected to gradient urea (7-5-3-2-1 mol/L, each gradient for 4 hours) dialysis at 4 degrees under protection from light to be renatured, and was finally dialyzed into physiological saline. After the reaction was complete, resultant HFn-Dox nanoparticles were passed through a Superdex 200 10/300 GL molecular sieve for purification to obtain monodispersed monomer nanoparticles for further analysis. FIG. 1a is a schematic diagram of loading a drug Doxorubicin into a targeting drug carrier (i.e., HFn protein) using a method of urea.

For cryo-electron microscopy characterization of the HFn nanoparticle loaded with a drug, after samples of HFn protein and HFn-Dox having the same concentration (20 μL, 0.25 mg/mL) were embedded with FEI Vitrobot Mark VI (FEI, Oregon), characterization was performed on the samples using a cryo-electron microscope FEI 300-kV Titan Krios (FEI, Oregon) equipped with a Gatan UltraScan4000 (model 895) 16-megapixel CCD lens. Nanoparticles of HFn protein and HFn-Dox were image under a condition of 96,000-time magnification, and electron beams in each visual field were about 20 e⁻/Å. FIG. 1b is a cryo-electron microscopy characterization graph of HFn protein before and after loading a drug. As a result, it was found that there was substantially no difference between the conformation of HFn-Dox and that of HFn protein before loading a drug.

Dynamic light scattering characterization of HFn protein before and after loading a drug was finished on DynaPro Titan (Wyatt Technology) with temperature control. Equal amounts of HFn protein and HFn-Dox were measured under a condition of 25° C. FIG. 1c is characterization performed on HFn protein before and after loading a drug using a dynamic light scattering method. It was found that HFn-Dox had good dispersibility and uniform particle size after loading a drug, and there was substantially no difference from HFn protein.

Example 2. Study on In Vitro Release and Stability of a Nanoscale Drug Carrier HFn-Dox Loaded with a Drug (1) In order to study the stability of a targeting drug carrier HFn-Dox loaded with a drug, we put Hfn-Dox nanoparticles (500 μmol/L, in terms of the amount of Dox, 500 μL) into a dialysis tube D-tube with a molecular weight cutoff of 6-8 kDa (Novagen) and then into physiological saline or normal mouse serum for incubation at 37° C. Samples were taken at incubation times of 0, 1, 2, 4, 8, 12, 24, 36, 48, 60 hours respectively, and the amount of Doxorubicin was measured using a HPLC method. Measured results were represented by dissociation percentages. Drug retention percentage=100%−dissociation percentage.

Figure 2:
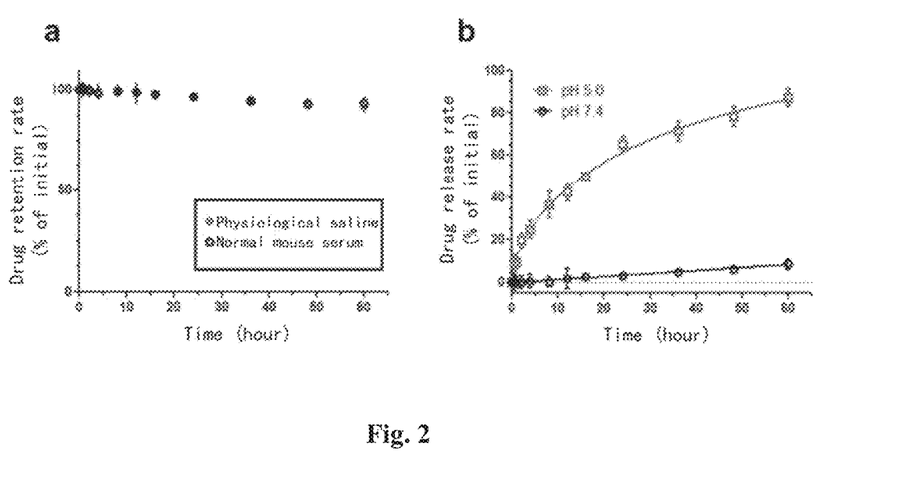
FIG. 2 shows a stability study of a targeting nanocarrier loaded with a drug (HFn-Dox)

The result was as shown in FIG. 2a, and the result of the stability test indicated that the Hfn-Dox drug carrier system was very stable in mouse serum under a condition of 37° C. Less than 10% was dissociated after 60 hours. This indicated that Hfn-Dox may be stably present in mouse serum after being administered to a mouse through the tail vein.

(2) In order to study the drug release behavior of HFn-Dox, by using PBS at pH 7.4 to simulate a physiological condition and using an acetic acid buffer at pH 5.0 to simulate an intracellular lysosome environment, we put HFn-Dox nanoparticles (500 μmol/L, in terms of the amount of Dox, 500 μL) into a dialysis tube D-tube with a molecular weight cutoff of 6-8 kDa (Novagen) and into PBS and the acetic acid buffer respectively for incubation under a condition of 37° C. Samples were taken at incubation times of 0, 1, 2, 4, 8, 12, 24, 36, 48, 60 hours respectively, and the amount of Doxorubicin was measured using a HPLC method. Measured results were represented by dissociation percentages of the drug.

The result was as shown in FIG. 2b. All of Doxorubicin loaded in the HFn protein shell was released after being incubated under a condition of pH 5.0 for 60 hours, whereas there was substantially no release under a physiological condition. Therefore, the drug release form of the carrier HFn-Dox loaded with a drug depended on the condition of the pH value.

Example 3. Study on In Vitro and In Vivo Targeting of a Nanoscale Drug Carrier HFn-Dox Loaded with a Chemotherapeutic Drug to Tumor Cells In order to study whether the in vitro and in vivo targeting of a drug carrier HFn protein shell to tumor cells was influenced before and after loading a chemotherapeutic drug Doxorubicin, typical human colorectal cancer cells HT-29 (ATCC: HTB-38) were selected for study. HT-29 tumor cells and bionic ferritin labeled with fluorescent molecules were incubated in vitro, and the binding of the bionic ferritin and tumor cells was detected using a flow cytometric and laser confocal method. A tumor-bearing mouse was administered by tail vein injection, using HFn-Dox nanoparticles labeled with radioactive $^{125}$I in vivo. Whether the targeting of radiolabeled HFn-Dox in vivo to HT-29 implanted tumor was influenced was further studied.

Figure 3:
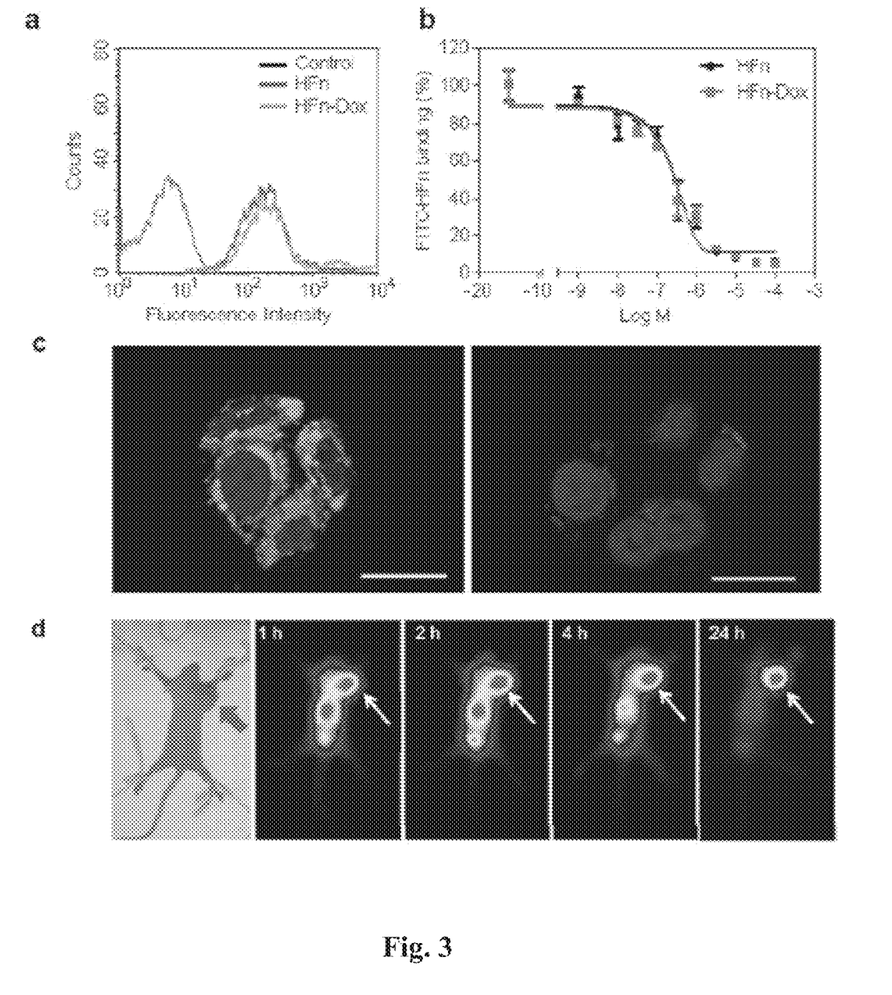
FIG. 3 shows a study in which specific targeting to tumor cells was achieved by a targeting nanocarrier loaded with a drug (HFn-Dox nanoparticle) through its receptor TfR1 in vitro and in vivo.

The experimental method was as follows. According to the labeling method provided in the instruction, an empty HFn protein shell and an HFn-Dox protein shell loaded with a drug were labeled with NHS-activated Cy 5.5 (Cy 5.5-NHS, purchased from GE Healthcare). HT-29 cells were cultured to about $1 \times 10^5$, and digested with trypsin. The cells were washed with 0.3% BSA/PBS, 50 μg/ml of HFn protein particles and HFn-Dox protein nanoparticles labeled with Cy 5.5 were added, and incubation was performed at 4° C. for 45 minutes. The cells were then washed with 0.3% BSA/PBS for three times, and finally re-suspended in PBS. Samples were tested for fluorescence by flow cytometry. The result was as shown in FIG. 3a. The binding of HFn-Dox to tumor cells HT-29 after loading Doxorubicin was not different from that of the HFn protein shell before loading the drug. That is, the binding of the HFn protein shell to tumor cells was not influenced by the operation of loading Doxorubicin to HFn through urea denaturation and renaturation.

In order to quantitatively study the binding abilities of HFn-Dox and HFn protein with tumor cells, a suitable concentration of FITC-labeled HFn was selected to perform a competition binding inhibition test. Likewise, cells were digested with trypsin when cultured to about $1 \times 10^5$. After washing with a buffer, a certain concentration of FITC-labeled HFn, excessive unlabeled HFn, and unlabeled HFn-Dox loaded with a Doxorubicin were added simultaneously, incubated at 4° C. for 45 minutes, washed for three times, and finally re-suspended in PBS. Samples were tested for fluorescence by flow cytometry. The result was as shown in FIG. 3b. Most of the binding of labeled HFn to cells can be competed off by excessive unlabeled HFn protein and HFn-Dox, and competitive inhibition curves were almost the same. It was further demonstrated that the binding of HFn-Dox with cancer cells is specific, and there were no difference between the binding abilities of HFn protein and HFn-Dox with tumor cells.

Literature (Li et al., *Proc. Natl. Acad. Sci. USA.* 2010) reported that a receptor of human H ferritin was TfR1. In order to confirm that TfR1 mediates the interaction of HFn-Dox with cancer cells, we used excessive anti-TfR1 antibodies to compete with FITC-labeled HFn-Dox for a cell surface receptor. The specific experimental method was as follows. Tumor cells HT-29 growing on glass coverslips (BD Biosciences) were placed in a six-well plate and cultured to a density of about 60%, and then the experiment began. Excessive mouse anti-human TfR1 antibodies CD71 (purchased from BD Pharmingen) and FITC-labeled HFn-Dox were added together, or FITC-labeled HFn-Dox was added separately, and incubation was performed at 37° C. for 45 minutes. The cells were washed with 0.3% BSA/PBS for three times, and finally fixed with 4% paraformaldehyde. After washing with PBS for three times, the nuclei were stained with DAPI (Roche Applied Science) for 10 minutes. After washing with PBS for another three times, a mounting agent for preventing fluorescence quenching was used for mounting. Laser confocal (Olympus FluoView FV-1000, Tokyo, Japan) observation was performed. Results can be seen in FIG. 3c. Most of the binding of FITC-labeled HFn-Dox with tumor cells HT-29 may be specifically competed off by an anti-TfR1 antibody, which demonstrated that TfR1 mediated the interaction of HFn-Dox with cancer cells.

In order to study the targeting of HFn-Dox in vivo to implanted tumor HT-29, HFn was first labeled with $^{125}$I using an Iodo-gen method. Labeled solution was purified via a PD-10 column and then measured for radiochemical purity. The labeling rate of $^{125}$I-HFn was ~78.1%, and the radiochemical purity after purification was >98.0%. 100 μL of a $^{125}$I-HFn-Dox physiological saline dilution was injected to a HT-29 tumor-bearing mouse through the tail vein (400 µCi, containing about 18.5 µg protein), and planar γ imaging was performed using single-photon emission computed tomography at 1, 2, 4, and 24 h respectively after injection. The result was as shown in FIG. 3d. HFn-Dox nanoparticles labeled with radioactive $^{125}$I rapidly aggregated at a tumor site, and the tumor can be clearly imaged at 1 h after injection. Non-specific aggregations in other organs are rapidly removed by in vivo metabolism within 24 hours. This indicated that HFn-Dox nanoparticles not only can highly specifically target tumor tissues in the body of a mouse, but also non-specific bindings in other organs may be rapidly discharged from the body through metabolism. That is, this H-ferritin nanoscale drug carrier that we newly developed can specifically delivery a loaded drug to the tumor site in vivo, can be effectively removed in healthy organs at the meanwhile, so as to prevent toxic side effects on healthy organs.

Example 4. Study on Mechanism of Nanoscale Drug Carrier HFn-Dox Killing Tumor Cells The principle of chemotherapeutic drug Doxorubicin molecules killing tumor was that Doxorubicin molecules were embedded in the double helix of DNA after entering the cell nucleus to inhibit the replication and transcription of DNA, such that tumor cells were induced to apoptosis. That is, the prerequisite for Doxorubicin exerting an effect of killing tumor was being capable of entering the cell nucleus of a tumor cell. In order to study whether HFn-Dox can release Doxorubicin loaded therein and pass it into the cell nucleus in the process and after entering a cell, we carried out observation using fluorescence-labeled HFn-Dox and a laser confocal means.

Figure 4:
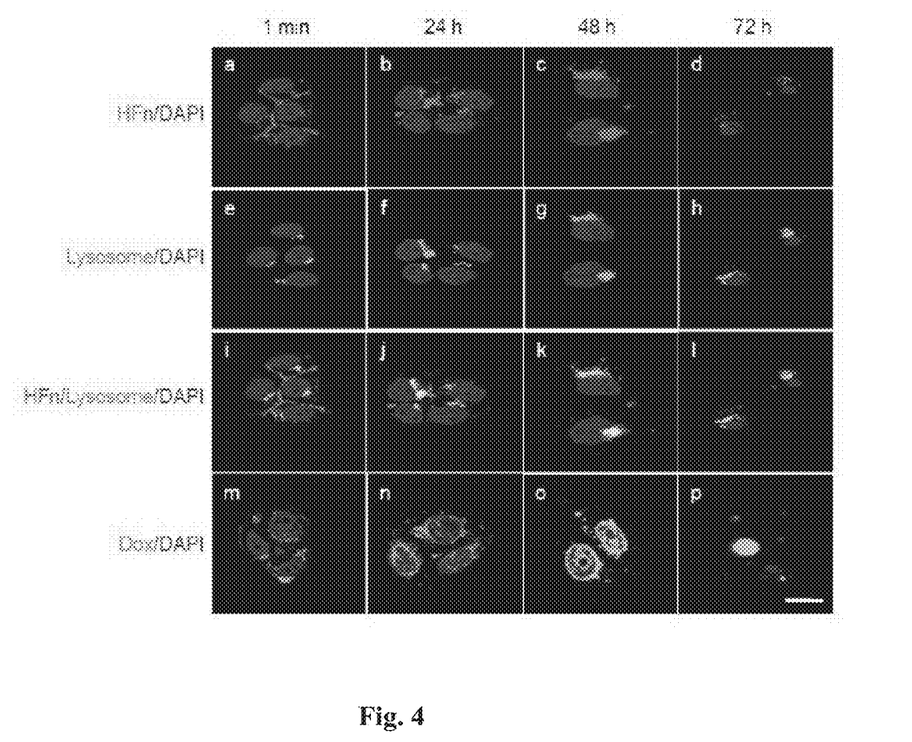
FIG. 4 shows a laser confocal study on the process of HFn-Dox entering the interior of a cell, wherein a protein shell is labeled with Cy 5.5; a marker molecule LAMP-1 of the lysosome is labeled with Alexa-488; and a fluorescence signal of Dox itself is observed.

A specific example was as follows. HFn-Dox nanoparticles were first subjected to Cy 5.5 modification. HT-29 cells growing on glass coverslips were cultured for 12 hour, and were incubated with 1 µM Cy 5.5-HFn-Dox in an incubator for 1 minute, 24 hours, 48 hours, and 72 hours respectively. After washing with PBS for three times, 4% paraformaldehyde was used for fixing for 5 minutes. 0.1% Triton X-100 was then used to permeabilize cells. After washing with PBS again, cells were blocked with 5% sheep serum at room temperature for 30 minutes. Alexa-488 labeled lysosome marker molecule Lamp1 antibodies (1:200, clone H4A3; Invitrogen) were then incubated at 37° C. for 1 hour. Finally, the nuclei were stained with DAPI (1 µg/mL, Roche Applied Science) for 10 minutes. Finally, observation was performed using a laser confocal microscope (Olympus FluoView FV-1000, Tokyo, Japan). The result was as shown in FIG. 4. The protein shell in the HFn-Dox nanoparticle was labeled with Cy 5.5, a marker molecule LAMP-1 of the lysosome was labeled with Alexa-488; and fluorescence signal of Dox itself was observed. By observing the behavior of HFn in a cell, we found that HFn, after binding to a receptor on the membrane protein, was subjected to endocytosis mediated by the receptor, transported into an endosome, and finally passed into a lysosome. This was consistent with those reported in a document (Li, L. et al., *Proc Natl Acad Sci USA*, 2010). After binding to a receptor TfR1 on a tumor cell, HFn-Dox nanoparticles are transported into an endosome and are finally passed into a lysosome, which is the same case as HFn. HFn-Dox nanoparticles were then degraded. The HFn protein shell was degraded to amino acid fragments, and released Dox was free out of the lysosome and was finally passed into the cell nucleus so as to exert killing effect on a tumor cell.

Figure 5:
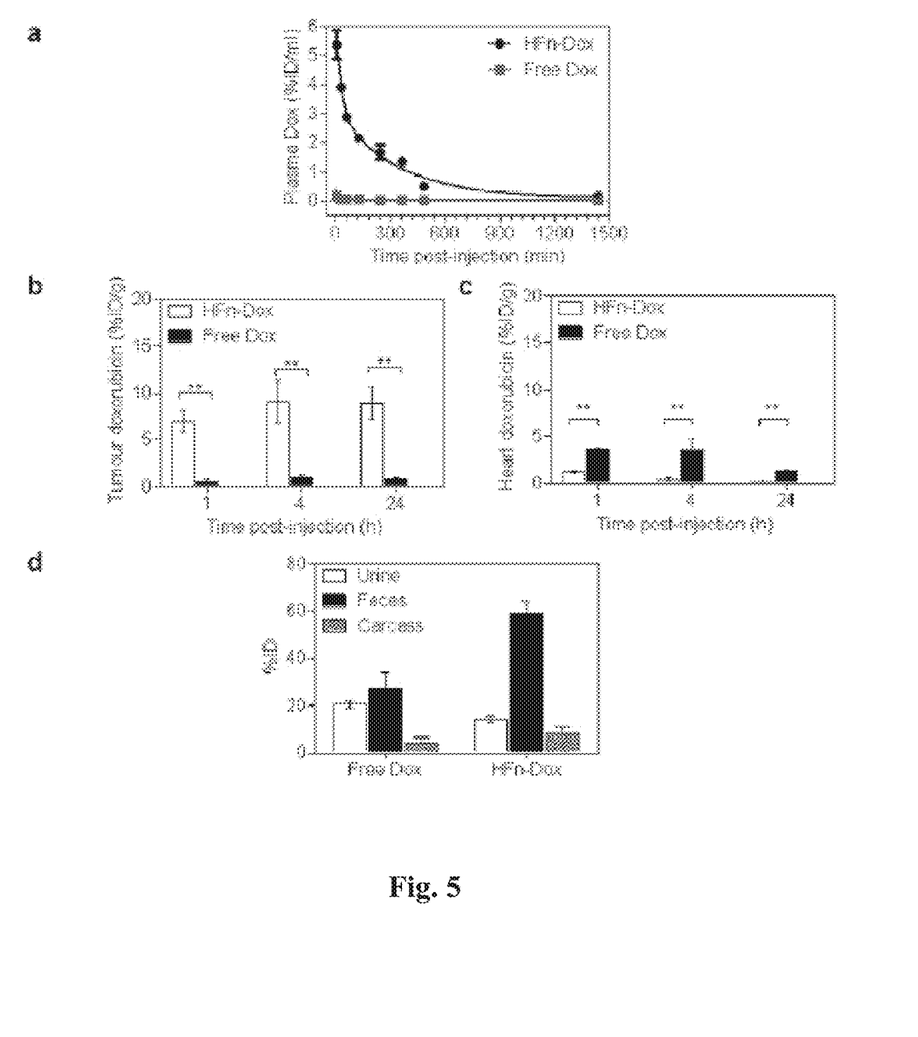
FIG. 5 shows a study on the in vivo pharmacokinetics, the tissue distribution, and the removal in vivo of HFn-Dox nanoparticles.

Example 5. Study on In Vivo Pharmacokinetics of a Tumor-Targeted Nanoscale Drug Carrier In order to study in vivo pharmacokinetics of HFn-Dox and compare it to free Doxorubicin, we injected free Doxorubicin and HFn-Dox nanoparticles having equal amounts of Doxorubicin (10 mg/kg mouse body weight) to female BALB/c mice through the tail vein (6 mice per group). Then, at 5 minutes, 30 minutes, 1 hour, 2 hours, 4 hours, 8 hours, 10 hours, and 24 hours after administration, 10-15 µL blood samples of mice were taken in a manner of venous blood sampling and were immediately added to a PBS buffer containing heparin (1000 U/mL). Next, we used an acidic isopropanol extraction method to measure the contents of Doxorubicin in blood samples. After uniformly mixed with acidic isopropanol, the blood samples were placed at −20° C. under protection from light and extracted overnight. The extract was then thoroughly oscillated. After centrifugation, the supernatant was placed in an opaque 96-well plate (Corning). Specific fluorescence readouts of Doxorubicin in the blood samples were measured on a fluorescence reader (Varioskan Flash Spectral Scanning Multimode Reader, ThermoFisher Scientific) using an excitation wavelength of 485 nm and an emission wavelength of 590 nm. The contents of Doxorubicin in the blood samples were measured by a fluorescence value curve with a standard Doxorubicin sample. The result was as shown in FIG. 5a. It was found in the study on in vivo pharmacokinetic of HFn-Dox nanoparticles in mice that the blood half-life of Dox packaged by human H-ferritin in the group injected with HFn-Dox nanoparticles was 12.2 times that of the group injected with free Doxorubicin under the condition of injecting equal amounts of Dox. The area under the curve (AUC) of blood half-life concentration-time of the HFn-Dox group was 209 times that of the free Doxorubicin group. Such a significant increase of blood half-life and a larger area under the curve demonstrated that HFn-Dox nanoparticles had a longer drug retention time in a systemic circulation. This enabled drugs to sustainably aggregate at the tumor site.

Example 6. Study on In Vivo Distribution of a Tumor-Targeted Nanoscale Drug Carrier Results in vitro and in vivo pharmacokinetics indicated that HFn-Dox was capable of effectively killing tumor cells in vitro and had a good behavior of in vivo metabolism. Then, can HFn-Dox specifically aggregate at the tumor site in vivo? In order to further study this issue, we performed the study on in vivo distribution of HFn-Dox.

A specific example was as follows. 24 BALB/c nude mice bearing HT-29 implanted tumor were randomly divided into two groups (free Doxorubicin processed group and HFn-Dox administered group). When tumor volume (volume=0.5×length×width×width) was up to 300 square millimeters, a test began. Free Doxorubicin and HFn-Dox having equal amounts of Doxorubicin (10 mg/kg mouse body weight) were injected to the two groups of mice. Mice were then sacrificed at 1 hour, 4 hours, and 24 hours after administration (4 mice at each time point), tumor, blood samples, and main tissues and organs were taken. The contents of Doxorubicin in blood samples were measured using an acidic isopropanol extraction method. As for the measurement of the contents of Doxorubicin in tumor and tissues, the following treatment was employed. Tumor or organs and tissues were weighed and then homogenized. All operations were finished on ice and in an environment under protection from light. 100 µL of homogenate was taken and subjected to an acidic isopropanol extraction treatment. The method for measured the concentration of Doxorubicin was the same as that in the part of in vivo pharmacokinetics. The results were as shown in FIGS. 5b and 5c. In the case that equal dosages of Dox were injected to mice bearing HT-29 implanted tumor, there were significant difference between an HFn-Dox nanoparticle administered group and a free Dox administered group in the accumulated amount of Dox within intracorporeal organs and tumor tissues. After the HFn-Dox administered group was administered, the content of Dox in tumor is ten times or more that of the free Dox administered group. After H-ferritin was used as a drug carrier for loading Doxorubicin, the noticeable increased content of Dox at the tumor site was a result influenced by comprehensive factors of long blood half-life, active tumor targeting, and receptor-mediated endocytosis of HFn-Dox nanoparticles. It was equally important that HFn-Dox nanoparticles significantly reduced the accumulated amount of Dox in healthy organs after H-ferritin shell loaded Doxorubicin. In particular, the concentration of Dox in the heart organ was greatly reduced by packaging Dox in H-ferritin, and was reduced by approximately 7.8 folds compared to free Dox, such that the severe toxicity of Dox drugs to the heart was reduced. Enrichment in tumor sites and reduced distribution in healthy organs of the chemotherapeutic drug Dox sufficiently indicated that H-ferritin was a highly effective Dox drug carrier.

It can be seen from FIG. 3d that nanoparticles which did not target the tumor site was rapidly removed from the body. In order to study and clarify in which pathway HFn-Dox was discharged from the body, an elimination experiment of drugs in mice was performed. A specific example was as follows. 10 healthy BALB/c mice were randomly divided into two groups. All of the mice were bred in metabolic cages. Equal dosages of free Doxorubicin and HFn-Dox (10 mg/kg mouse body weight) were injected to the two groups of mice through the tail vein. In the process of breeding, urine and manure of the mice were collected. After culturing for 24 hours, the mice were sacrificed, and main tissues and organs were taken. The contents of Doxorubicin in all feces and main tissues and organs of the mice were measured using an acidic isopropanol extraction method. The result was as shown in FIG. 5d, it was found in a further study on HFn-Dox nanoparticles in the metabolism of healthy mice that a large part of the drug was discharged from the body through manure and urine and very little was retained in the body. It was further confirmed that HFn-Dox nanoparticles may be effectively discharged from the body by healthy intracorporeal organs so as to prevent toxic side effects on healthy organs.

Example 7. Study on Anti-Tumor Pharmacodynamics of Tumor-Targeted Nanoscale Drug Carrier HFn-Dox As a tumor-targeted nanoscale drug carrier, the most direct effect of examination was killing and inhibitory effects on tumor. A specific example was as follows. 40 female BALB/c nude mice bearing HT-29 implanted tumor were randomly divided into five groups. When the volume of the implanted tumor was up to about 100 square millimeters, drugs were injected to all of tumor-bearing mice through the tail vein. Here, a PBS group and an HFn protein group were control groups. A free Doxorubicin group, an HFn-Dox group, and a clinically used liposomal Doxorubicin drug Doxil group were administered groups. Since the maximal tolerated dosage of mice to free Doxorubicin was 5 mg/kg mouse body weight, the administration dosage of the free Doxorubicin group was 5 mg/kg mouse body weight. The administration amount of HFn-Dox was 20 mg/kg mouse body weight. In order to quantitatively comparatively study side effects of Doxil and HFn-Dox, the injection dosage of Doxil was also 20 mg/kg mouse body weight. Measurements of body weights and tumors of mice were three times per week. In the process of therapy, a mouse will be sacrificed if the mouse had a body weight decrease more than 15% or a tumor volume more than 1000 square millimeters.

Figure 6:
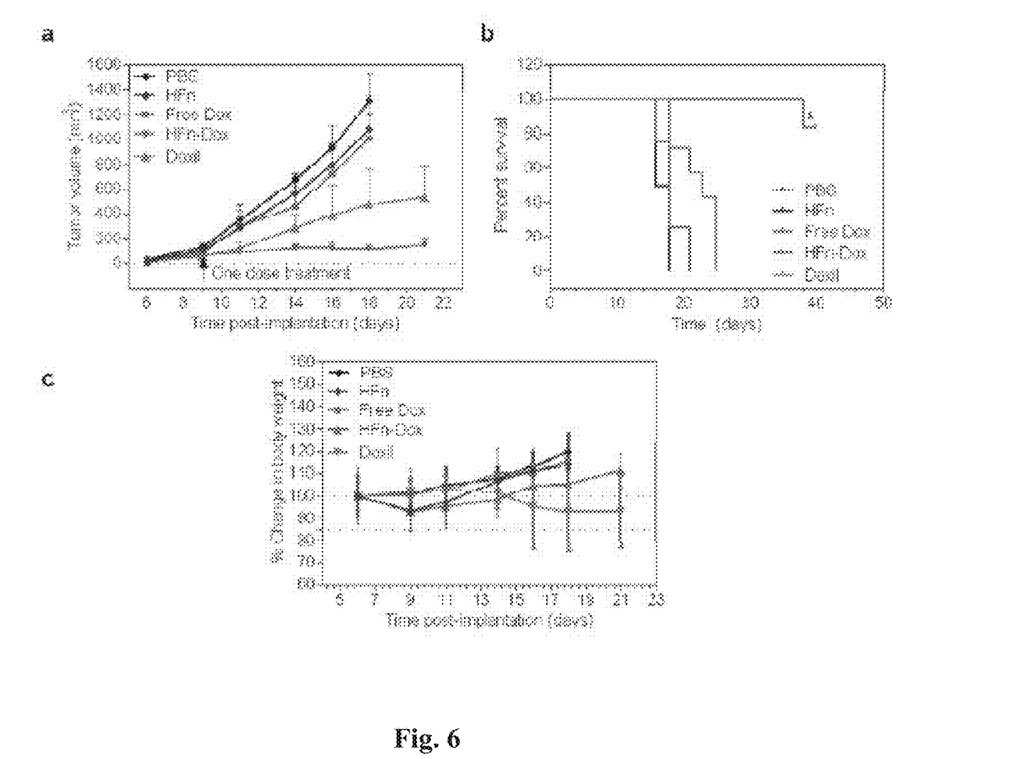
FIG. 6 shows therapeutic effects of HFn-Dox nanoparticles loaded Doxorubicin on colorectal cancer of nude mice.

The experimental result was as shown in FIG. 6. In the therapy of a cancer patient, the dosage of administration and the number of administration were very important. However, bound by toxic side effects of chemotherapeutic drugs, the therapy of cancer usually became administration in a small amount at a high frequency. However, administration in a small amount at a high frequency usually failed to effectively kill tumor cells. Therefore, it is also a development trend of drug carriers, if it is capable of enhancing the tolerated dosage of an organism to chemotherapeutic drugs, i.e., reducing toxic side effects of chemotherapeutic drugs. Through experiments, researchers found that the maximal tolerated dosage of mice to HFn-Dox was 20 mg/kg by Dox equivalent and the maximal tolerated dosage to free Doxorubicin was 5 mg/kg, as for healthy mice in the case of single administration. This indicated that H-ferritin as a drug carrier not only had targeting and reduced toxic side effects on organs, but also may increase the tolerated dosage of mice to Dox by 4 times.

As shown in FIG. 6a, tumor growths of the free Doxorubicin administered group, the PBS group, and H-ferritin shell group were very fast, and average tumor volumes had already exceeded 1000 $mm^3$ on day 18. As for the mice treated in the group in which HFn-Dox nanoparticles were administered in the maximal tolerated dosage (20 mg/kg by Dox equivalent), the growth of tumor was significantly inhibited during observation, Liposomal Doxorubicin Doxil, which was a clinical chemotherapeutic drug, had very high toxic side effects on mice under the condition of the same dosage as HFn-Dox. As shown in FIGS. 6b and 6c, the body weights of mice significantly decreased after one dose of Doxil. As the time increased, the body weight decreased more. Compared to the control groups, although Doxil exhibits a significant tumor-inhibiting effect, the survival time was not significantly improved yet due to its side effects. Average survival times of tumor-bearing mice in PBS, free Dox, and H-ferritin shell administered groups were 17, 18, 18 days, respectively. Doxil processed group was 23 days. The therapy with single administration at the maximal tolerated dosage of mice to free Doxorubicin (5 mg/kg) had almost no inhibitory effect on the growth of tumor. In contrast, in a 40-day experimental window, single administration of HFn-Dox nanoparticles at the maximal tolerated dosage significantly inhibited the growth of tumor. Therefore, by using H-ferritin as a drug carrier of a chemotherapeutic drug Dox, a significantly tumor-inhibiting effect can be achieved merely by means of single administration.

In the process of cancer therapy, the therapeutic effect of cancer will be improved by precisely delivering drugs to the site of lesion and reducing toxic side effects of chemotherapeutic drugs. It is confirmed by the disclosure that a natural human H-ferritin nanoparticle having a cavity with an inner diameter of 8 nm may delivery a high dosage of a chemotherapeutic drug Dox to the tumor site and can significantly inhibit the growth of tumor with merely single administration. This natural nanoscale drug carrier exhibits ideal physicochemical properties and highly specific tumor targeting, and can improve the anti-tumor effect by increasing the accumulated amount of the drug at a tumor site at the same time of reducing toxic side effects of the chemotherapeutic drug Dox.

Compared to nanoscale drug delivery carriers (Jain, K. K. Bmc Med, 2010), liposomes (Doxil) or polymer nanoparticles, which have been widely used in clinical therapy, the human H-ferritin nanocarrier described in the disclosure has the following advantages. (1) Active targeting: A natural H-ferritin nanoparticle may deliver Dox to a tumor cell by the specific binding with a receptor TfR1 highly expressed on the surface of a tumor cell through a receptor-mediated endocytic pathway without any functionalized modification of a ligand. Compared to many clinically commonly-used polymer or liposome drug delivery carriers, this active tumor-targeted property and the receptor-mediated endocytic mechanism enable drugs to be specifically retained and absorbed at a tumor site so as to have a high-concentration drug distribution in the tumor and be capable of effectively inhibiting the growth of tumor (FIG. 6a). Most of conventional nanoscale drug carriers achieve the delivery of a therapeutic drug to a tumor site by passive enhanced permeability and retention effect (EPR). This passive targeting therapeutic strategy usually exhibits a limited therapeutic effect and may cause seepage of drugs and induce the generation of drug resistance (Barenholz, Y. J Control Release, 2012; Wang, R. B. et al., J Nanomater, 2013; Kieler-Ferguson, H. M. et al. Wires Nanomed Nanobi, 2013). (2) Good pharmacokinetic feature and safety: Compared to free Doxorubicin, the HFn-Dox nanoparticle exhibits a longer blood half-life and a higher AUC accumulation as well as a higher drug accumulation in tumor and a lower drug distribution in healthy organs, and can be finally discharged from healthy tissues. When treating tumor, these features enable HFn-Dox nanoparticles to be capable of greatly improving the therapeutic effect of tumor at the same time of reducing toxic side effects of drugs. More importantly, H-ferritin is a protein naturally present in human bodies and does not contain any potential toxic component, and thus it does not irritate inflammation or immune response of an organism and exhibits an excellent biocompatibility. (3) Excellent anti-tumor activity: HFn-Dox nanoparticles can inhibit the growth of tumor by means of merely single injection therapy. This therapeutic effect is much more effective than clinically commonly-used polymer or liposome drug carriers. Conventional nanoscale drug carriers usually need several dosages of therapy to achieve the object of inhibiting tumor growth (Tang, N. et al., J Natl Cancer Inst, 2007; Kaminskas, L. M. et al., Mol Phartnaceut, 2012; Hrkach, J. et al., Sci Transl Med, 2012). (4) Amenable to production and purification in a large batch. A natural H-ferritin nanocarrier is absolutely a protein expressed by E. coli through gene recombination, and has a high expression level and is amenable to be purified (Fan, K. et al, Nat Nanotechnol, 2012). Its active tumor-targeted property enables the modification with a ligand or the adjustment of physicochemical properties to be unnecessary so as to prevent the artificial modification process, which has the features of being complex and usually high-cost, low production, poor reproducibility, etc. In addition to this, the loading of Dox into an H-ferritin nanocage may be achieved by simply operating depolymerization-polymerization of the ferritin shell. The synthesis process of the HFn-Dox nanoparticle of the disclosure will easily achieve standard drug production conditions required in applications at clinical levels. We believe that these unique properties enable the H-ferritin nanoparticle of the disclosure to become an ideal tumor-targeted drug delivery carrier.

REFERENCES

1. Fan, K. et al., Magnetoferritin nanoparticles for targeting and visualizing tumour tissues. Nat Nanotechnol 7, 459-464 (2012).
2. Dreher, M. R. et al., Tumor vascular permeability, accumulation, and penetration of macromolecular drug carriers. J Natl Cancer 198, 335-344 (2006).
3. Kim, M. et al., pH-dependent structures of ferritin and apoferritin in solution: disassembly and reassembly. Biomacromolecules 12, 1629-1640 (2011),
4. Yang, S. C., Ge, H. X., Hu, Y., Jiang, X. Q. & Yang, C. Z. Doxorubicin-loaded poly(butylcyanoacrylate) nanoparticles produced by emulsifier-free emulsion polymerization. J Appl Polym Sci 78, 517-526 (2000).
5. Harrison, P. M. & Arosio, P. The ferritins: molecular properties, iron storage function and cellular regulation. Biochim Biophys Acta 1275, 161-203 (1996).
6. Li, L. et al., Binding and uptake of H-ferritin are mediated by human transferrin receptor-1. Proc Natl Acad Sci USA 107, 3505-3510 (2010).
7. Jain, K. K. Advances in the field of nanooncology. Bmc Med 8 (2010).
8. Barenholz, Y. Doxil (R)—The first FDA-approved nanodrug: Lessons learned. Journal of Controlled Release 160, 117-134 (2012).
9. Wang, R. B., Billone, P. S. & Mullett, W. M. Nanomedicine in Action: An Overview of Cancer Nanomedicine on the Market and in Clinical Trials. J Nanomater (2013).
10. Kieler-Ferguson, H. M., Frechet, J. M. J. & Szoka, F. C. Clinical developments of chemotherapeutic nanomedicines: polymers and liposomes for delivery of camptothecins and platinum (II) drugs. Wires Nanomed Nanobi 5, 130-138 (2013).
11. Tang, N. et al., Improving penetration in tumors with nanoassemblies of phospholipids and doxorubicin. J. Natl Cancer Inst 99, 1004-1015 (2007).
12. Kaminskas, L. M. et al., Doxorubicin-Conjugated PEGylated Dendrimers Show Similar Tumoricidal Activity but Lower Systemic Toxicity When Compared to PEGylated Liposome and Solution Formulations in Mouse and Rat Tumor Models. Mol Pharmaceut 9, 422-432 (2012).
13. Hrkach, J. et al., Preclinical development and clinical translation of a PSMA-targeted docetaxel nanoparticle with a differentiated pharmacological profile. Sci Transl Med4, 128ra139 (2012).

What is claimed is:

1. A tumor-targeted drug delivery system, comprising a tumor-targeted drug carrier and a tumor-treating drug, wherein the tumor-targeted drug carrier is stable in physiological saline and comprises full heavy-chain human ferritin,
   wherein the full heavy-chain human ferritin is polymerized to form a nanoparticle having a cavity, and the tumor-treating drug is loaded in the cavity,
   wherein the system is prepared by:
   depolymerizing a polymerized full heavy-chain human ferritin;

adding the tumor-treating drug to the depolymerized full heavy-chain human ferritin so as to bind the tumor-treating drug to the depolymerized full heavy-chain human ferritin; and re-polymerizing the depolymerized full heavy-chain human ferritin bound with the tumor-treating drug to form a nanoparticle, and wherein the full heavy-chain human ferritin is depolymerized with a high concentration of urea, and the depolymerized full heavy-chain human ferritin is re-polymerized by using a concentration gradient of urea, where the concentration gradient of urea gradually decreases to zero.

2. The system of claim 1, wherein the tumor treating drug is used for the treatment of malignant tumors and cancers of human bodies.

3. The system of claim 2, wherein the tumor-treating drug is used for the treatment of colorectal cancer.

4. The system of claim 1, wherein the tumor treating drug is selected from chemotherapeutic drugs, radioisotopes, cytokines, nucleic acids, anti-tumor drugs, or anti-inflammatory drugs.

5. A method for preparing a tumor-targeted drug delivery system, comprising:

depolymerizing a polymerized full heavy-chain human ferritin;

adding a tumor-treating drug to the depolymerized full heavy-chain human ferritin so as to bind the tumor-treating drug to the depolymerized full heavy-chain human ferritin; and re-polymerizing the depolymerized full heavy-chain human ferritin bound with the tumor-treating drug to form a nanoparticle, wherein the full heavy-chain human ferritin is depolymerized under a condition of a high concentration of urea, and the depolymerized full heavy-chain human ferritin is re-polymerized by using a gradient of the concentration of urea gradually decreasing to zero.

6. The system of claim 1, wherein the tumor-treating drug is used for the treatment of colorectal cancer, lung cancer, breast cancer, ovarian cancer, melanoma, gastric cancer, pancreatic cancer, bladder cancer, renal cancer, prostate cancer, brain cancer and various hematological cancers.

7. The system of claim 1, wherein the tumor-treating drug is used for the treatment of Hodgkin's disease, non-Hodgkin's lymphoma, and leukemia.

8. The system of claim 1, wherein the tumor-treating drug is Doxorubicin.

* * * * *